United States Patent [19]

Leathers et al.

[11] Patent Number: 4,940,463
[45] Date of Patent: Jul. 10, 1990

[54] DISPOSABLE COMBINED PANTY WITH SANITARY NAPKIN

[76] Inventors: Sherman Leathers, 1104 E. 55th St., Brooklyn, N.Y. 11234; Geronimo C. Williamson, 535 Lafayette Ave., Brooklyn, N.Y. 11205

[21] Appl. No.: 15,240
[22] Filed: Feb. 17, 1987
[51] Int. Cl.$^5$ ............................................. A61F 13/16
[52] U.S. Cl. ..................................... 604/396; 604/393
[58] Field of Search ................ 604/386, 387, 390–393, 604/395–402, 358, 377, 394, 385, 354, 391; 2/400, 402, 406

[56] References Cited

U.S. PATENT DOCUMENTS

| 1,233,811 | 7/1917 | Roger | 604/401 |
| 2,206,412 | 7/1940 | Levy | 2/406 |
| 2,450,789 | 7/1945 | Frieman | 604/397 |
| 2,748,772 | 6/1956 | Titone et al. | 2/404 |
| 2,977,957 | 4/1961 | Clyne | 604/396 |
| 3,207,158 | 9/1965 | Yoshitake et al. | 604/394 |
| 3,254,648 | 6/1966 | Greiner et al. | 604/358 |
| 3,294,090 | 12/1966 | Younger | 604/385.1 |
| 3,424,162 | 1/1969 | Parravicini | 604/396 |
| 3,599,638 | 8/1971 | Rickard | 604/396 |
| 3,669,114 | 6/1972 | Morane | 604/377 |
| 3,860,003 | 1/1975 | Buell | 604/385 A |
| 3,955,575 | 5/1976 | Okuda | 604/391 |
| 4,216,773 | 8/1980 | Ryan | 604/385.1 |
| 4,427,408 | 1/1984 | Karami et al. | 2/402 |

FOREIGN PATENT DOCUMENTS 2356948  5/1975  Fed. Rep. of Germany .......... 2/406

Primary Examiner—C. Fred Rosenbaum
Assistant Examiner—Sharon Rose
Attorney, Agent, or Firm—Goodman & Teitelbaum

[57] ABSTRACT

A disposable panty having a tubular body portion with an hour-glass configuration to provide an intermediate crotch portion and opposing front and rear waist portions. A sanitary napkin is disposed within the crotch portion between the outer and inner layers of the body portion. A ribbon member passes through the front and rear waist portions to secure the pantry to the wearer, where the ends of the ribbon member are removably secured together. The sanitary napkin includes a frame member provided with absorbent balls disposed in the opening of the frame member to increase the absorption of the menstrual discharge. A flexible liquid impervious material is disposed between the outer layer of the body portion and the sanitary napkin to prevent the passage of the menstrual discharge to the outer layer. The panty with the sanitary napkin can be folded upon itself to function solely as a sanitary napkin.

10 Claims, 2 Drawing Sheets

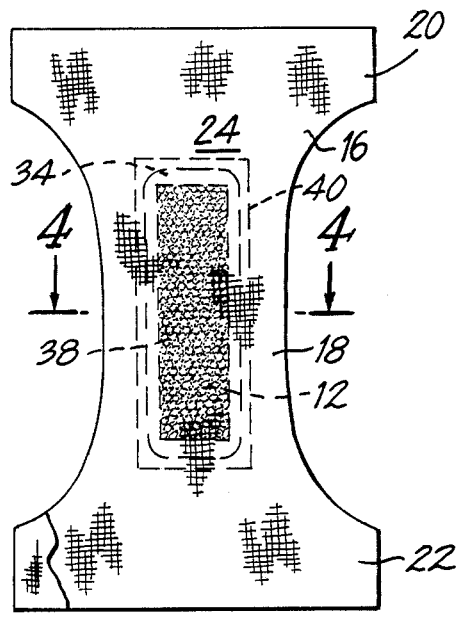
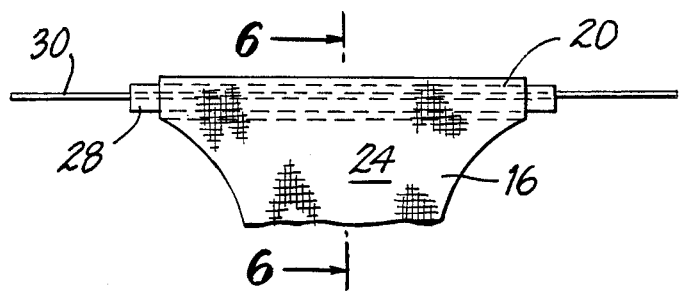
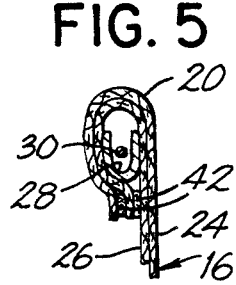
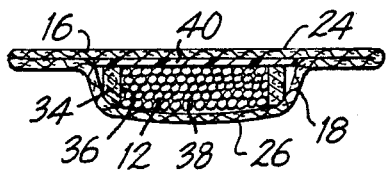
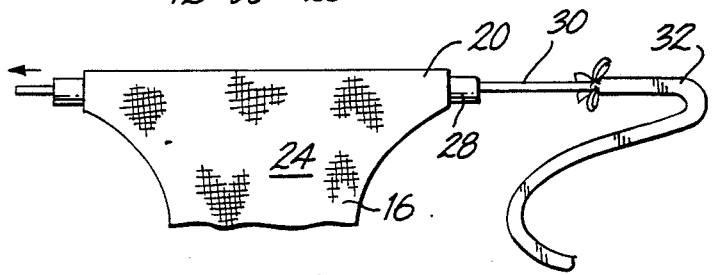
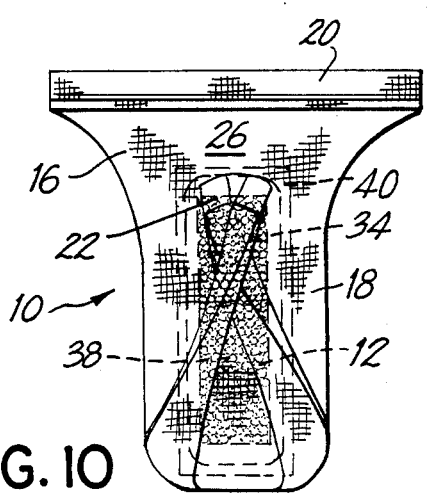
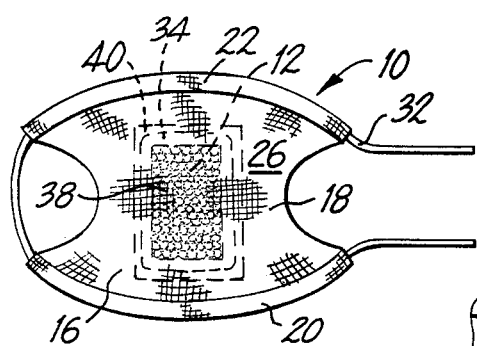
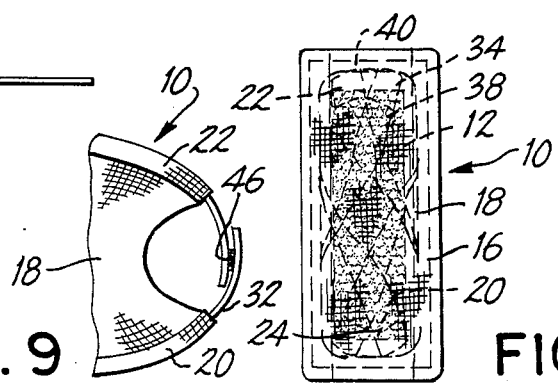
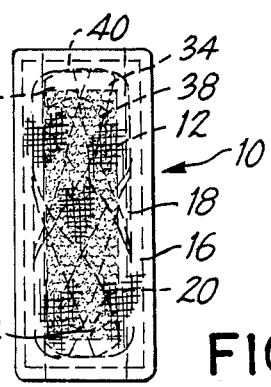

DISPOSABLE COMBINED PANTY WITH SANITARY NAPKIN

BACKGROUND OF THE INVENTION

This invention relates to underpants, especially panties, and more particularly to a disposable panty provided with a sanitary napkin in the crotch area thereof.

Disposable panties provided with sanitary napkins are well known in the art, where for hygienic reasons it is desired to throw such panties away after having been used only once. These prior art panties have a conventional construction including an expensive material which is seamed at its sides to provide a waist opening and two leg openings. Elastic bands are usually sewn around the waist and leg openings so that a single panty size will fit a number of different sized users.

However, in many cases, the material used to form the panty is not really inexpensive, and the method of manufacturing the panty is difficult and expensive, so that because of the costs thereof, many so-called disposable panties are in fact too expensive to be thrown away after only one use, thereby reducing the hygienic value thereof.

It is further noted, that these prior art disposable panties do not fit well and are a discomfort to the user, so that their only value is in the disposable diaper art, where they are not readily usable by teenage and adult woman users.

Furthermore, many of the sanitary napkins provided in these disposable diapers do not effectively absorb the menstrual discharge and retain same, so that the sanitary napkin is of little or no value to the wearer thereof.

U.S. Pat. Nos. 2,748,772, 3,424,162 and 4,427,408 disclose a disposable panty provided with a sanitary napkin or an absorbent pad sewn into the crotch area. U.S. Pat. No. 3,599,638 also discloses a disposable panty, where the crotch area is formed with a pocket to receive the sanitary napkin. Each of these patents disclose a conventional panty provided with an elasticized waistband and elasticized leg openings, where each panty has at least one side seam for the construction thereof.

It is further noted, that U.S. Pat. No. 3,860,003 discloses a disposable diaper having an hour-glass shape with elastic strips secured to the crotch portions of the diaper to provide for securement thereof over the legs of an infant so that the child's discharged fluid does not run down along the child's legs.

SUMMARY OF THE INVENTION

Accordingly, it is an object of the present invention to provide a disposable combined panty with sanitary napkin which overcomes the disadvantages of the prior art disposable articles.

Another object of the present invention is to provide a disposable combined panty with sanitary napkin which can be fabricated from an inexpensive material, and which can be manufactured at a low cost, and which is comfortable to wear.

A further object of the present invention is to provide a disposable combined panty with sanitary napkin of the type described above which permits the panty to be fabricated from a tubular material so that the sanitary napkin is disposed within the tubular material.

Yet another object of the present invention is to provide a disposable combined panty with sanitary napkin of the type described above which permits the panty to have an hour-glass shape.

Yet a further object of the present invention is to provide a disposable combined panty with sanitary napkin of the type described above which permits the panty to be of the bikini type.

Another object of the present invention is to provide a disposable combined panty with sanitary napkin of the type described above which permits the panty to be secured to the wearer by a ribbon member passing through the front and rear waist portions of the panty.

And yet a further object of the present invention is to provide a disposable combined panty with sanitary napkin which permits the sanitary napkin to have a frame member provided with absorbent balls disposed therein for increased effective absorption of the menstrual discharge and for retaining same.

Another object of the present invention is to provide a disposable combined panty with sanitary napkin of the type described above which has a flexible liquid impervious material disposed on an outer surface of the sanitary napkin to prevent the passage of the menstrual discharge to the outer wall of the panty.

And still yet another object of the present invention is to provide a disposable combined panty with sanitary napkin which can be folded upon itself to function solely as a sanitary napkin.

Briefly, in accordance with the present invention, there is provided a disposable panty including a tubular body portion having an hour-glass configuration to provide an intermediate crotch portion and opposing front and rear waist portions, with a sanitary napkin disposed within the crotch portion between the outer and inner layers of the body portion. A ribbon member passes through the front and rear waist portions to secure the panty to the wearer, where the ends of the ribbon member can either be tied together on the wearer's waist, or be secured together by an adhesive. The sanitary napkin includes a frame member provided with absorbent balls disposed in the opening thereof to increase the absorption of the menstrual discharge. A flexible liquid impervious material is disposed between the outer layer of the body portion and the sanitary napkin to prevent the passage of the menstrual discharge to the outer layer. The panty with the sanitary napkin can be folded upon itself to function solely as a sanitary napkin.

BRIEF DESCRIPTION OF THE DRAWING

With the above and additional objects and advantages in view, as will hereinafter appear, this invention comprises the devices, combinations and arrangements of parts hereinafter described, by way of example, and illustrated in the accompanying drawings of a preferred embodiment in which:

FIG. 3 is an elevational view showing the sanitary napkin disposed within the crotch portion of the panty;

FIG. 4 is a sectional view taken along line 4—4 of FIG. 3;

FIG. 5 is a fragmented elevational view showing a waist band portion of the panty;

FIG. 6 is a sectional view taken along line 6—6 of FIG. 5;

FIG. 7 is a fragmented elevational view similar to FIG. 5, showing the ribbon member about to be inserted into the waist band portion;

FIG. 8 is a top elevational view of the panty after the ribbon member has been inserted through both waist band portions;

FIG. 9 is a fragmented top elevational view, showing a modified way of securing the ends of the ribbon member together;

FIG. 10 is an elevational view, showing one of the waist band portions being folded onto the crotch portion of the panty; and FIG. 11 is an elevational view showing the panty in a folded condition.

In the various figures of the drawings, like reference characters designate like parts.

DESCRIPTION OF THE PREFERRED EMBODIMENT

Figure 1:
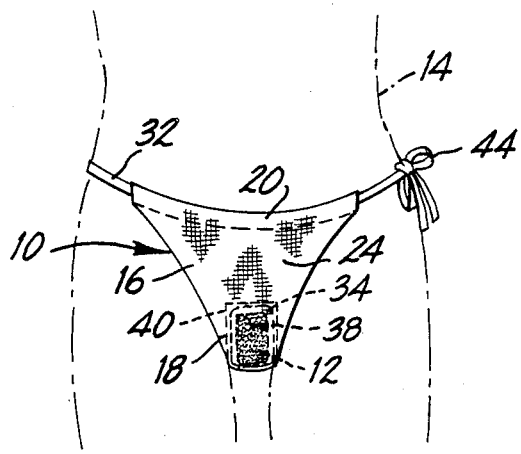
FIG. 1 is a front elevational view of a disposable combined panty with sanitary napkin in accordance with the present invention, showing the panty being worn by the user.

Referring now to the drawings, FIG. 1 shows a disposable panty 10 combined with a sanitary napkin 12 being worn by a user or wearer 14 shown in phantom lines. Accordingly, the panty 10 is of the bikini type so as to be comfortably worn by the user 14. The panty 10 includes an hour-glass shaped body portion 16 to provide an intermediate crotch portion 18 and opposing front waist band portion 20 and rear waist band portion 22, as shown best in FIG. 2. The body portion 16 is fabricated from a tubular material, being preferably a gauze material, to provide an outer layer 24 and an inner layer 26, as best shown in FIG. 4. The hour-glass shape can easily be obtained by laterally stretching out the front and rear waist band portions 20, 22, while squeezing in the crotch portion 18, where the gauze material readily permits such stretching and squeezing thereof to maintain the hour-glass shape. Accordingly, the panty material can be cotton, paper, plastic and like material.

Figure 2:
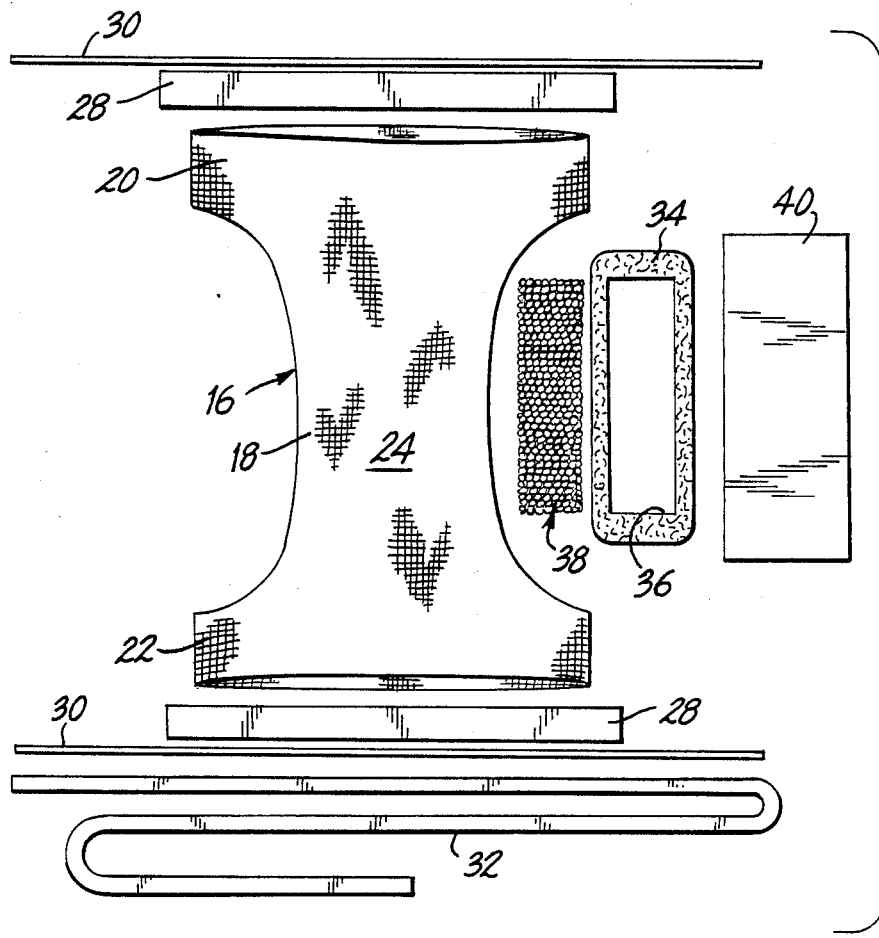
FIG. 2 is an exploded elevational view showing the separate parts of the disposable combined panty with sanitary napkin.

FIG. 2 further shows a pair of band members 28 and a pair of strings 30, together with a ribbon member 32, which are inserted into the front and rear waist band portions 20, 22, respectively, in a manner set forth below.

FIG. 2 also shows the sanitary napkin 12 to include a frame member 34 having an opening 36 therein for receiving a plurality of small absorbent balls or spheres 38. The frame member 34 is flexible to conform to the body shape of the wearer 14, as indicated in FIGS. 1 and 8. Preferably, both the frame member 34 and the absorbent balls 38 are fabricated from cotton in order to absorb the menstrual discharge, where the absorbent balls 38 have a high degree of absorption. The absorbent balls 38 are pressed into the opening 36 of the frame member 34 so that the frame member 34 holds the absorbent balls 38 together in a compact arrangement, as best shown in FIG. 4.

FIG. 2 additionally shows a sheet 40 of flexible, liquid impervious material, preferably plastic, to prevent the passage of the menstrual discharge therethrough.

As shown in FIGS. 3 and 4, the sanitary napkin 12, comprising the frame member 34 and absorbent balls 38, is inserted into the panty body member 16 and positioned in the crotch portion 18 so that the sanitary napkin 12 is disposed between the outer layer 24 and inner layer 26 of the panty 10. Additionally, the sheet 40 is disposed against the sanitary napkin 12 so that the sheet 40 lies between the sanitary napkin 12 and the outer layer 24 of the panty 10 to thus prevent the passage of the menstrual discharge to the outer layer 24.

After the sanitary napkin 12 and sheet 40 have been inserted into the tubular body portion 16, each band member 28 and associated string 30 are positioned on their respective front and rear waist band portions 20, 22. The front and rear waist band portions 20, 22 are then each folded upon themselves. During this process the band members 28 are also folded on themselves so that the strings 30 are positioned within the folded members as best shown in FIGS. 5 and 6.

As shown in FIG. 6, the front waist band 20, and also the rear waist band 22, are folded inwardly towards the crotch portion 18, while the band portions 28 are folded outwardly from the crotch portion 18 so that each string 30 is completely enclosed between the fold line of each front and rear waist band portion 20, 22 and the fold line of each band member 30. The edge of both the front waist band 20 and the rear waist band 22 are secured in place in the folded condition by adhesive 42, as shown in FIG. 6, where it is understood that other securement means could also be used, such as by stitching. It is noted, for appearance, that the edges of the front and rear waist bands 20, 22 are folded against the inner layer 26 of the panty 10.

Preferably, when the user purchases the panty 10, the ribbon member 32 is not secured therein, where the ribbon member 32 can be made in several decorative colors so that several ribbon members 32 of different colors can be purchased with the panty 10. Accordingly, after the user has selected the desired colored ribbon member 32, the selected ribbon member 32 is inserted into the panty 10 as shown in FIG. 7. The user 14 ties one end of the ribbon member 32 to one of the strings 30 and pulls the other end of the string 30 to pass the ribbon member 32 through one of the folded waist bands 20, 22 so that the ribbon member 32 lies within the folded band member 28 therein. The user now again ties the same end of the ribbon member 32 to the other string 30 and repeats the above step to insert the ribbon member 32 through the other one of the waist bands 20, 22 so that the ribbon member 32 now lies within the other folded band member 28 therein, as shown in FIG. 8. The pair of strings 30 can now be discarded.

The ribbon member 32 is preferably fabricated from an elastic or stretchable material so that when the ends of the ribbon member are tied together, such as by making a bow 44 as shown in FIG. 1, the ribbon member 32 will be tightly held against the user 14. Alternatively, the ends of the ribbon member 32 can be provided with a commercially available self-adhesive 46, as shown in FIG. 9, so that it would not be necessary to tie the end of the ribbon member 32 together as mentioned above.

Alternatively, instead of wearing the panty 10 as shown in FIG. 1, the user 14 can fold the panty 10 as shown in FIG. 10 and 11, and use the panty 10 in the folded condition as a conventional sanitary napkin. FIG. 10 shows one of the waist bands, such as the rear waist band 22, being folded onto the crotch portion 18, whereby the other of the waist bands, such as the front waist band 20, can then also be folded onto the crotch portion 18 on top of the first-folded rear waist band 22. Thereafter, the sides of the crotch portion 18 are also folded in to obtain the rectangular shape shown in FIG. 11, to define a conventional looking sanitary napkin, which can now be used by the user 14 in a conventional manner.

There has been disclosed heretofore the best embodiment of the invention presently contemplated. However, it is to be understood that various changes and modifications may be made thereto without departing from the spirit of the present invention.

What is claimed is:

1. A disposable panty comprising:
   a tubular body portion to provide outer and inner layers with said inner layer being disposable against a wearer thereof;
   said tubular body portion having an hour-glass configuration to provide an intermediate narrow crotch portion and opposing front and rear wide waist band portions;
   a sanitary napkin to absorb menstrual discharge of the wearer being disposed within said crotch portion between said outer and inner layers of said tubular body portion;
   a liquid impervious sheet disposed between said sanitary napkin and said outer layer to prevent passage of the menstrual discharge to said outer layer;
   said sanitary napkin including a frame member having a central opening therethrough extending from a first side to an opposing second side of said frame member, and absorbent means disposed within said central opening in a compact arrangement;
   said first side of said frame member being positioned against said inner layer, and said second side of said frame member being positioned against said liquid impervious sheet;
   first surfaces of said absorbent means being disposed against said inner layer, and second surfaces of said absorbent means being disposed against said liquid impervious sheet;
   said absorbent means comprising a plurality of absorbent balls; and
   securing means for securing said front and rear waist bans portions to the wearer to provide a bikini type panty.

2. A disposable panty according to claim 1, wherein said tubular body portion is fabricated from a gauze material, and said absorbent balls are fabricated from cotton.

3. A disposable panty according to claim 1, wherein said front and rear waist band portions are each secured in a folded condition on themselves with said securing means passing through each of said folded front and rear waist band portions.

4. A disposable panty according to claim 3, wherein said securing means is a ribbon member.

5. A disposable panty according to claim 4, wherein ends of said ribbon member are tied together to secure said panty to the wearer.

6. A disposable panty according to claim 4, wherein ends of said ribbon member are secured together by an adhesive to secure said panty to the wearer.

7. A disposable panty according to claim 4, wherein a folded band member is disposed within each of said folded front and rear waist band portions to receive said ribbon member.

8. A disposable panty according to claim 7, wherein string means are disposed through each of said folded band members to draw said ribbon member therethrough.

9. A disposable panty according to claim 7, wherein said tubular body is fabricated from a gauzy material, and said absorbent balls are fabricated from cotton.

10. A disposable panty according to claim 1, wherein said tubular body is fabricated from a gauze material.

* * * * *